(12) United States Patent
Bataille

(10) Patent No.: US 12,178,395 B2
(45) Date of Patent: Dec. 31, 2024

(54) CATHETER, SHEATH OR DILATOR FOR HEART VALVE DECALCIFICATION TREATMENT AND METHOD OF USE THEREOF

(71) Applicant: NORTH STAR MEDICAL INC., Montréal (CA)

(72) Inventor: Olivier Bataille, Lachine (CA)

( * ) Notice: Subject to any disclaimer, the term of this patent is extended or adjusted under 35 U.S.C. 154(b) by 305 days.

(21) Appl. No.: 17/641,965

(22) PCT Filed: Sep. 10, 2020

(86) PCT No.: PCT/CA2020/051217
§ 371 (c)(1),
(2) Date: Mar. 10, 2022

(87) PCT Pub. No.: WO2021/046643
PCT Pub. Date: Mar. 18, 2021

(65) Prior Publication Data
US 2022/0304749 A1 Sep. 29, 2022

Related U.S. Application Data

(60) Provisional application No. 62/898,738, filed on Sep. 11, 2019.

(51) Int. Cl.
*A61B 1/00* (2006.01)
*A61B 5/00* (2006.01)
(Continued)

(52) U.S. Cl.
CPC ........ *A61B 1/00135* (2013.01); *A61B 5/0036* (2018.08); *A61B 5/0066* (2013.01);
(Continued)

(58) Field of Classification Search
CPC ... A61B 5/0036; A61B 5/0066; A61B 5/0084; A61B 18/245; A61B 2018/0022;
(Continued)

(56) References Cited

U.S. PATENT DOCUMENTS 5,190,050 A * 3/1993 Nitzsche ........... A61M 25/0144
600/585
5,192,278 A 3/1993 Hayes et al.
(Continued)

OTHER PUBLICATIONS

Davi [Continuous Wave (CW) and Pulsed Laser Effects on Vascular Tissues and Occlusive Disease In Vitro, Lasers in Surgery and Medicine 9239-250 (1985)]. (Year: 1985).*
(Continued)

*Primary Examiner* — Oommen Jacob
(74) *Attorney, Agent, or Firm* — Anglehart et al.

(57) ABSTRACT

A deflectable sheath or dilator or catheter used for cardiac procedures; it has a shaft with one or more lumens; an optical fiber for use in channeling light used for visualization of calcification, heart tissue architecture or the progress of the cardiac procedure; the sheath or dilator or catheter includes an additional optical fiber for use as part of an ultrafast laser for calcium removal on or in heart valve tissue or for performing surgical intervention of the heart, or where the optical fiber is configurable for propagating a photon beam as part of an ultrafast laser for removing calcium on or in heart valve tissue or for performing surgical intervention of the heart.

13 Claims, 17 Drawing Sheets

(51) Int. Cl.
*A61B 18/00* (2006.01)
*A61B 18/22* (2006.01)
*A61B 18/24* (2006.01)
*A61M 1/00* (2006.01)
*A61M 25/10* (2013.01)

(52) U.S. Cl.
CPC .......... *A61B 5/0084* (2013.01); *A61B 18/245* (2013.01); *A61M 1/84* (2021.05); *A61B 2018/0022* (2013.01); *A61B 2018/00369* (2013.01); *A61B 2018/00904* (2013.01); *A61B 2018/00982* (2013.01); *A61B 2018/2227* (2013.01); *A61B 2218/007* (2013.01); *A61B 2562/0233* (2013.01); *A61M 2025/1056* (2013.01)

(58) Field of Classification Search
CPC ........... A61B 2018/00369; A61B 2018/00904; A61B 2018/00982; A61B 2018/2227; A61B 2218/007; A61B 2562/0233; A61B 18/24; A61B 1/00135; A61B 2017/00057; A61B 1/00165; A61M 2025/1056
See application file for complete search history.

(56) References Cited

U.S. PATENT DOCUMENTS

| | | | |
|---|---|---|---|
| 5,350,375 A | 9/1994 | Deckelbaum et al. | |
| 5,443,446 A | 8/1995 | Shturman | |
| 5,749,890 A * | 5/1998 | Shaknovich | A61F 2/958 606/198 |
| 5,815,627 A * | 9/1998 | Harrington | G02B 6/032 385/125 |
| 6,440,125 B1 | 8/2002 | Rentrop | |
| 6,942,657 B2 | 9/2005 | Sinofsky et al. | |
| 7,742,805 B2 * | 6/2010 | Furnish | A61B 5/02007 600/478 |
| 8,083,707 B2 | 12/2011 | Tosaya et al. | |
| 8,182,530 B2 | 5/2012 | Huber | |
| 8,535,298 B1 | 9/2013 | Neev | |
| 9,271,794 B2 | 3/2016 | Tyc et al. | |
| 9,895,216 B2 | 2/2018 | Golan | |
| 10,219,780 B2 | 3/2019 | Castella et al. | |
| 10,305,244 B2 | 5/2019 | Sierra et al. | |
| 2005/0251116 A1 | 11/2005 | Steinke et al. | |
| 2006/0100553 A1 | 5/2006 | Lodin | |
| 2007/0078500 A1 * | 4/2007 | Ryan | A61B 5/6853 600/473 |
| 2008/0255433 A1 * | 10/2008 | Prough | A61B 5/0095 600/301 |
| 2009/0185191 A1 * | 7/2009 | Boppart | A61B 5/6852 356/479 |
| 2009/0216314 A1 * | 8/2009 | Quadri | A61F 2/915 623/1.16 |
| 2009/0264707 A1 * | 10/2009 | Hendriks | A61B 5/0059 600/181 |
| 2010/0292629 A1 * | 11/2010 | Dacey, Jr. | A61L 2/0011 607/2 |
| 2013/0023865 A1 * | 1/2013 | Steinke | A61B 5/0066 606/7 |
| 2015/0057648 A1 | 2/2015 | Swift et al. | |
| 2017/0014183 A1 * | 1/2017 | Gifford, III | A61B 17/320758 |
| 2017/0325943 A1 | 11/2017 | Robin et al. | |
| 2017/0333132 A1 | 11/2017 | Grace et al. | |
| 2018/0355157 A1 * | 12/2018 | Taira | G02B 6/4436 |
| 2019/0069916 A1 | 3/2019 | Hawkins et al. | |
| 2019/0133688 A1 * | 5/2019 | Feldman | A61B 1/00 |
| 2022/0304749 A1 * | 9/2022 | Bataille | A61B 18/24 |

OTHER PUBLICATIONS

International application No. PCT/CA2020/051217 International Search Report dated Nov. 30, 2020.
International application No. PCT/CA2020/051217 Search Strategy dated Nov. 30, 2020.
International application No. PCT/CA2020/051217 Written Opinion of the International Searching Authority dated Nov. 30, 2020.
Bjorn Wedel et al., "Industrial Fiber Beam Delivery System for Ultrafast Lasers", Laser Technik Journal, Apr. 2016, pp. 42-44.
Rohde, I., et al., "Resection of Calcified Aortic Heart Leaflets In Vitro by Q-Switched 2 μm Microsecond Laser Radiation." Journal of Cardiac Surgery 30.2 (2015): pp. 157-162.

* cited by examiner

CATHETER, SHEATH OR DILATOR FOR HEART VALVE DECALCIFICATION TREATMENT AND METHOD OF USE THEREOF The present application claims priority from U.S. provisional patent application No. 62/898,738 filed on Sep. 11, 2019, incorporated herein by reference.

TECHNICAL FIELD

The present disclosure relates to catheters and/or sheaths and/or dilator, and more particularly to catheters and/or sheaths and/or dilator used in cardiac procedures.

BACKGROUND

Valvular disease affects more than 100 million people worldwide. Degenerative aortic calcification in the elderly is the most common valve disease in developed countries, whereas rheumatic deterioration of the mitral and aortic valves is an endemic disease that affects young adults and children in the rest of the world. About 2,500,000 prosthetic heart valves are implanted in patients each year, with revenues of over $8 billion USD. The heart valve market is increasing at an average rate of 9% per year and has historically demonstrated cyclic fluctuation between mechanical and tissue valves. However, the demand for tissue valves, primarily focused on the elderly patient segment, has increased in recent years as this population is growing in western countries.

Emerging markets account for 80% of the market potential for heart valves and are experiencing double digit growth. There are currently no satisfactory long term solutions for valve replacement patients in these countries. Implantation of mechanical valves in young patients is challenging and costly due to the requirements of anti-coagulation management. In these markets, patients are able to access adequate medical facilities for the initial implantation; however, they frequently return to rural settings where anti-coagulation cannot be managed. As a consequence, the implantation of tissue valves in young adults is growing. However, these valves have a limited life expectancy due to calcification and structural deterioration and thus must be replaced within 10 to 15 years, mandating multiple replacements over the patient's expected lifetime, an economic deterrent for patients in developing countries.

At present, the only advance in the heart valve market is procedural. Catheter-based implantation of tissue valves is a less invasive technique that was proposed by interventional cardiologists in 2004 as a therapeutic option for inoperable, old and frail patients, a small but growing patient population. This is a welcome alternative and has enlarged the market for tissue valves. However, the durability of tissue valves compressed for delivery through small catheters is less than that of conventionally implanted tissue valves.

Some patients are not eligible for valve replacement and most valve replacement are not a perfect anatomical match; thus attempting the treat the native valve on this subset population may be a better clinical option.

After nearly 15 years of trans-catheter valve replacement, it can now be observed that animal tissue valves, synthetic tissue valves, and polymeric tissue valves implanted through such procedures show the same challenges as the previously used open heart surgery tissue valve replacement. Namely, they start to calcify after just 5 years and in most cases require surgical intervention after 10 to 15 years of implantation.

SUMMARY

Ultrafast lasers have been used in the laboratory environment to perform precise and with no heat affected zone for machining purposes. During the machining process, the particles from the laser cutting have been discovered to be of very small size, down to the nano-particles of various metals and other materials. In recent years, femtosecond lasers have utilized this feature to create aerosol and colloidal nano-particles. Colloidal gold nano-particles have been used in oncology for various medical and nutritional treatments.

During any cardiovascular procedure, some of the major concerns are thrombo-embolitic events, air embolism events, and the introduction of any particle in the cardiovascular system. However, it is typically understood that a particle under 1 micron introduced into the left side of the heart is not a risk to trigger a stroke or of any concern for the person.

A minimally invasive prophylactic and therapeutic decalcification provided on a regular basis (every 5 years or as required based on standard diagnostic techniques such as regurgitation factor) can be performed on the patient's native valve or implant in a standard cardiac catheter lab with the patient recovering within 24 hours and no removal of Trans Aortic Valve Implant (TAVI), valve over valve over valve (when an initial TAVI is implanted over the native valve and then a second TAVI in implanted over the initial TAVI) with just a small incision for femoral access and a transseptal puncture or a small sub-clavian approach. The same minimally invasive approach can also be used on the native valve if the patient's cardiac insufficiency is primarily due to native valve calcification.

Ultrafast laser pulverization may provide the advantage of having the pulverized particle size be very small, for example, to the scale of a nano particle. This may be so small that the clinical implication is insignificant and the particles will not cause embolisms.

As an ultrafast laser material processing is generally considered an a-thermal process, there may be no further concern about affecting the leaflet tissue and potentially losing its normal elasticity.

The present disclosure may be particularly well suited for embedded treatment and removal of deeply embedded calcium within the heart valve tissue. The optical coherence tomography technology can determine the location and depth at which calcium is embedded and the system can adapt the laser focal distance to effectively target and treat the calcification.

Furthermore, different materials can be better pulverized at certain pulse repetition rates, pulse durations, and wavelength and energy levels. As such the femto second laser can be pre-set at a certain range for automatic setting based on OCT feedback on calcification profile (characteristics of the calcification).

The present disclosure may provide clinicians the ability to perform minimally invasive surgery on a micro or nano scale to restore adequate valvular decalcification and tissue elasticity.

A broad aspect of the present disclosure is a deflectable sheath or dilator or catheter used for cardiac procedures. The deflectable sheath or dilator or catheter has a shaft with a proximal end and a distal end comprising one or more lumens running along a length of the shaft; an optical fiber located in one of the one or more lumens for use in channeling light used for visualization of calcification, heart tissue architecture or the progress of the cardiac procedure; wherein: the sheath or dilator or catheter further comprises an additional optical fiber for use as part of an ultrafast laser for calcium removal on or in heart valve tissue or for performing surgical intervention of the heart, the additional optical fiber running along a length of another of the one or more lumens; or the optical fiber is configurable for propagating a photon beam as part of an ultrafast laser for removing calcium on or in heart valve tissue or for performing surgical intervention of the heart.

In some embodiments, the deflectable sheath or dilator or catheter may include an inflatable balloon at the distal end of the shaft for pressing a heart valve leaflet in an open position.

In some embodiments, the deflectable sheath or dilator or catheter may include one or more pull wires running along a length of the shaft; and a steering mechanism for causing tension to be applied to or diminished from one or more of the one or more pull wires for steering the shaft, wherein each of the or more pull wires is connected or connectable to a steering mechanism.

In some embodiments, the deflectable sheath or dilator or catheter may include a handle joined to the proximal end of the shaft, wherein the steering mechanism is located in the handle and comprises an input component for allowing a user to manually actuate the steering mechanism.

In some embodiments, the deflectable sheath or dilator or catheter may include the steering and advancement mechanism is part of a surgical robot.

In some embodiments, the deflectable sheath or dilator or catheter may include an additional optical fiber for use as part of an ultrafast laser for calcium removal on or in heart valve tissue or for performing surgical intervention of the heart, the additional optical fiber running along a length of another of the one or more lumens.

In some embodiments, the additional optical fiber may be a hollow core optical fiber.

In some embodiments, the optical fiber may be configurable for propagating a photon beam as part of an ultrafast laser for removing calcium on or in heart valve tissue or for performing surgical intervention of the heart.

In some embodiments, the optical fiber may be a dual body optical fiber including an inner core and an outer core, wherein the outer core of the dual body optical fiber may be a hollow core optical fiber, wherein the visualization may be carried out by the inner core, and the calcium removal or the surgical intervention of the heart may be performed by photon energy transported by the outer core.

In some embodiments, the deflectable sheath or dilator or catheter may include a port for connecting the deflectable sheath or dilator or catheter to a vacuum source; and an additional lumen with a coaxial structure running along a length of the shaft for removing pulverized calcium or other debris through the additional lumen, or for securing a valve leaflet in an open position, when the deflectable sheath or dilator or catheter is connected to the vacuum source through the port.

In some embodiments, an end of the optical fiber used for visualization located at or near the distal end of the shaft may have a right-angle prism configuration.

In some embodiments, the deflectable sheath or dilator or catheter may include a controller that is configured to receive light information from light that was first emitted by the optical fiber, and perform optical coherence tomography based on the light information.

In some embodiments, the controller may be further configured to generate depth measurement data by performing the optical coherence tomography, the depth measurement data providing information on a location of a site for the surgical intervention or of the calcium deposit.

In some embodiments, the controller may be further configured to select regions for decalcification or for performing surgical intervention as a function of data obtained by the performing optical coherence tomography.

In some embodiments, the deflectable sheath or dilator or catheter may include an embolic filter.

In some embodiments, the deflectable sheath or dilator or catheter may include a power source for, when the sheath or dilator or catheter further comprises an additional optical fiber for use as part of an ultrafast laser, the ultrafast laser located in another of the one or more lumens, powering the ultrafast laser; or when the optical fiber is configurable for propagating a photon beam as part of an ultrafast laser, providing a source of power for generating the photon beam.

Another broad aspect is a kit for performing cardiac procedures. The kit includes a shaft of a catheter or sheath comprising, including one or more lumens running along a length of the shaft; and one or more pull wires running along a length of the shaft; and an optical fiber for visualization during the cardiac procedure, adapted to be inserted in one of the one or more lumens of the shaft.

In some embodiments, the optical fiber may be a dual body optical fiber with an outer core and an inner core such that the optical fiber is also used as part of an ultrafast laser for performing surgical interventions of the heart or for breaking down calcium deposits located on or in heart tissue, wherein the outer core of the dual body optical fiber may be a hollow core optical fiber, wherein the visualization may be carried out by the inner core, and calcium removal or surgical intervention may be performed by photon energy transported by the outer core.

In some embodiments, the kit may include a second optical fiber, wherein the second optical fiber may be a hollow core optical fiber, the second optical fiber insertable into another lumen of the one or more lumens, wherein the second optical fiber may be configurable to act as an ultrafast laser for performing surgical interventions of the heart or for breaking down calcium deposits located on or in heart tissue.

Another broad aspect is a method of decalcifying heart tissue or performing a surgical intervention directed at heart tissue. The method includes performing optical coherence tomography to visualize at least one of heart tissue and calcium deposited on or in heart tissue; targeting at least one of the calcium and a site to perform a surgical intervention of heart tissue by using visualization information obtained by the performing optical coherence tomography; and conducting at least one of removal of the targeted calcium and a surgical intervention directed at the targeted site of heart tissue using an ultrafast laser.

In some embodiments, the optical coherence tomography may be performed using information obtained from light channeled through an optical fiber.

In some embodiments, the using an ultrafast laser may include propagating photons through a hollow core optical fiber, generating a high power laser beam.

In some embodiments, the performing optical coherence tomography may generate distance information pertaining to at least one of the calcium and the site to perform a surgical intervention, where the method may include adjusting a focal distance of the ultrafast laser prior to the conducting at least one of removal of the targeted calcium and the surgical intervention.

In some embodiments, the method may include adjusting following properties of the ultrafast laser as a function of visualization information obtained by the performing optical coherence tomography: laser source; wavelength of light generated by the ultrafast laser; and/or pulse duration of the ultrafast laser.

In some embodiments, the method may include inflating a balloon to maintain a heart valve leaflet in an open position.

In some embodiments, the method may be performed for decalcifying heart valves.

In some embodiments, the ultrafast laser may include an optical fiber, and wherein the optical fiber of the ultrafast laser may be located in a lumen of a shaft of a sheath, catheter or dilator.

In some embodiments, the method may include removing pulverized calcium particles through a lumen of a shaft of a catheter, sheath or dilator using a vacuum.

In some embodiments, the method may include securing heart valve tissue to a portion of a catheter, sheath or dilator using a vacuum maintained through a lumen of the catheter, sheath or dilator by a vacuum source.

Another broad aspect is use of an optical fiber during a heart tissue decalcification procedure to generate light used to visualize calcium deposits on or in heart tissue by way of optical coherence tomography.

Another broad aspect is use of an ultrafast laser comprising an optical fiber for decalcifying heart tissue, wherein a laser beam propagates via the optical fiber to calcium deposits lodged on or in heart tissue, the removal of the calcium deposits performed by the laser beam, wherein the removal is an a-thermal process.

Another broad aspect is a method of removing pulverized calcium particles resulting from a heart tissue decalcification procedure, comprising removing the pulverized calcium deposits through a lumen located along a length of a shaft of a catheter, sheath or dilator by creating a vacuum in the lumen.

Another broad aspect is a method of securing heart tissue to a portion of a catheter, sheath or dilator during a cardiac procedure, comprising creating a vacuum in a lumen of a shaft of the catheter, sheath or dilator, the vacuum securing the heart tissue to the catheter, sheath or dilator.

In some embodiments, the heart tissue may be a valve leaflet.

Another broad aspect is a deflectable sheath or dilator or catheter used for cardiac procedures. The deflectable sheath or dilator or catheter includes a shaft with a proximal end and a distal end comprising one or more lumens running along a length of the shaft, wherein at least one of the one or more lumens has a coaxial structure, and a port for connecting the sheath, dilator or catheter to a vacuum source, wherein connecting the deflectable sheath or dilator or catheter to the vacuum source via the port creates a vacuum in the at least one of the one or more lumens for removing pulverized calcium particles or debris through the at least one of the one or more lumens; or for securing heart tissue to the deflectable sheath or dilator or catheter.

In some embodiments, the deflectable sheath or dilator or catheter may include the vacuum source.

the deflectable sheath or dilator or catheter may include an optical fiber running along a length of another of the one or more lumens, the optical fiber for use in channeling light used for visualization of calcification, heart tissue architecture or the progress of the cardiac procedure.

the deflectable sheath or dilator or catheter may include an inflatable balloon at the distal end of the shaft for pressing a heart valve leaflet in an open position.

Another broad aspect is a deflectable sheath or dilator or catheter used for cardiac procedures. The deflectable sheath or dilator or catheter has a shaft with a proximal end and a distal end comprising one or more lumens running along a length of the shaft; an optical fiber located in one of the one or more lumens for use in channeling light used for visualization of calcification, heart tissue architecture or the progress of the cardiac procedure; an inflatable balloon at the distal end of the shaft for pressing a heart valve leaflet in an open position; and a mechanical spiralling guidewire in contact with an inner surface of the balloon, the guidewire configured to propagate mechanical shockwaves to breakup calcium buildup on or in the heart tissue.

In some embodiments, the mechanical guidewire may be made from nitinol.

BRIEF DESCRIPTION OF THE DRAWINGS

The invention will be better understood by way of the following detailed description of embodiments of the invention with reference to the appended drawings, in which.

DETAILED DESCRIPTION

In the present disclosure, by "surgical intervention of the heart", it is meant a procedure that involves the removal or reshaping of heart tissue.

Figure 1A:
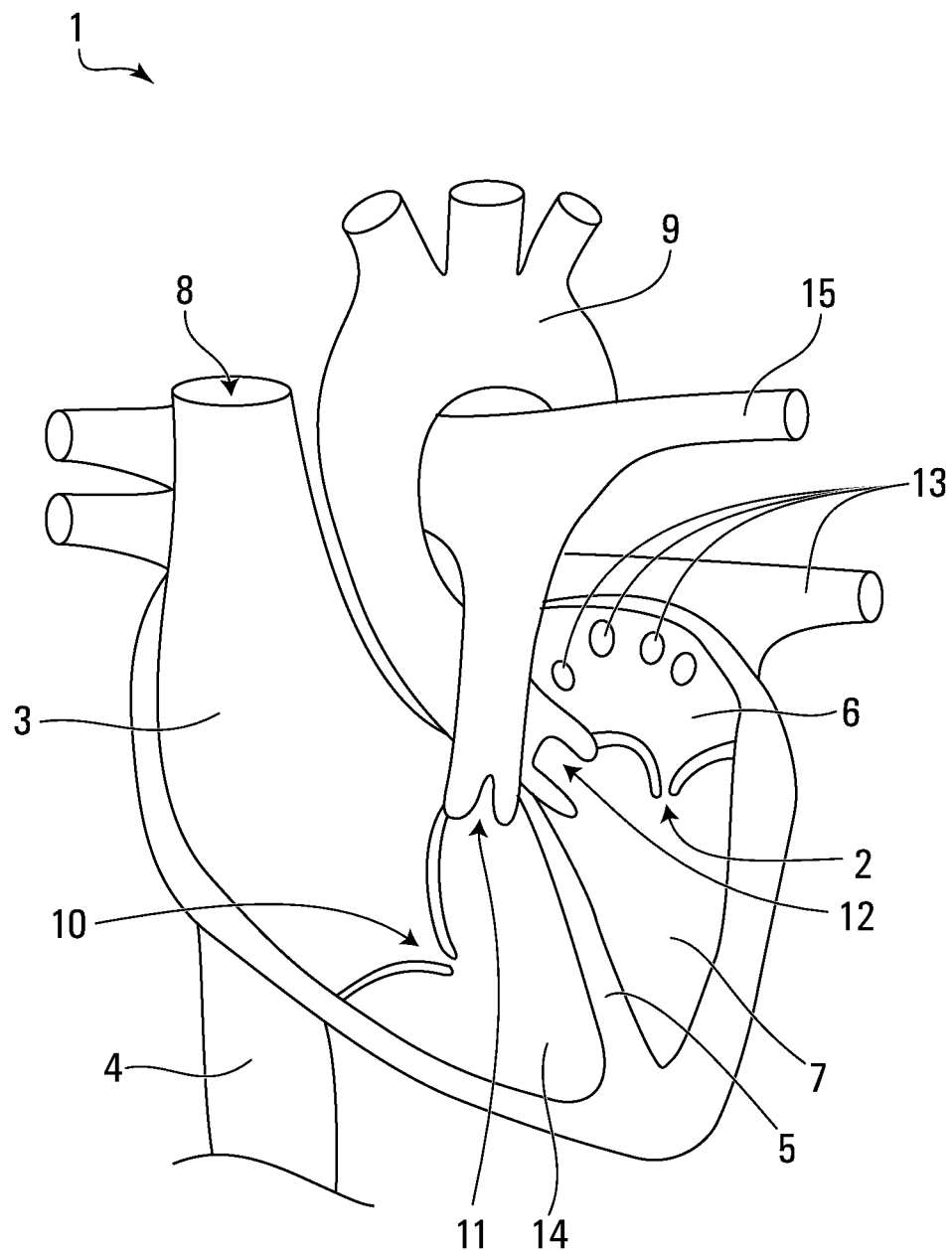
FIGS. 1a and 1b are schematic illustrations of the heart.
Figure 1B:
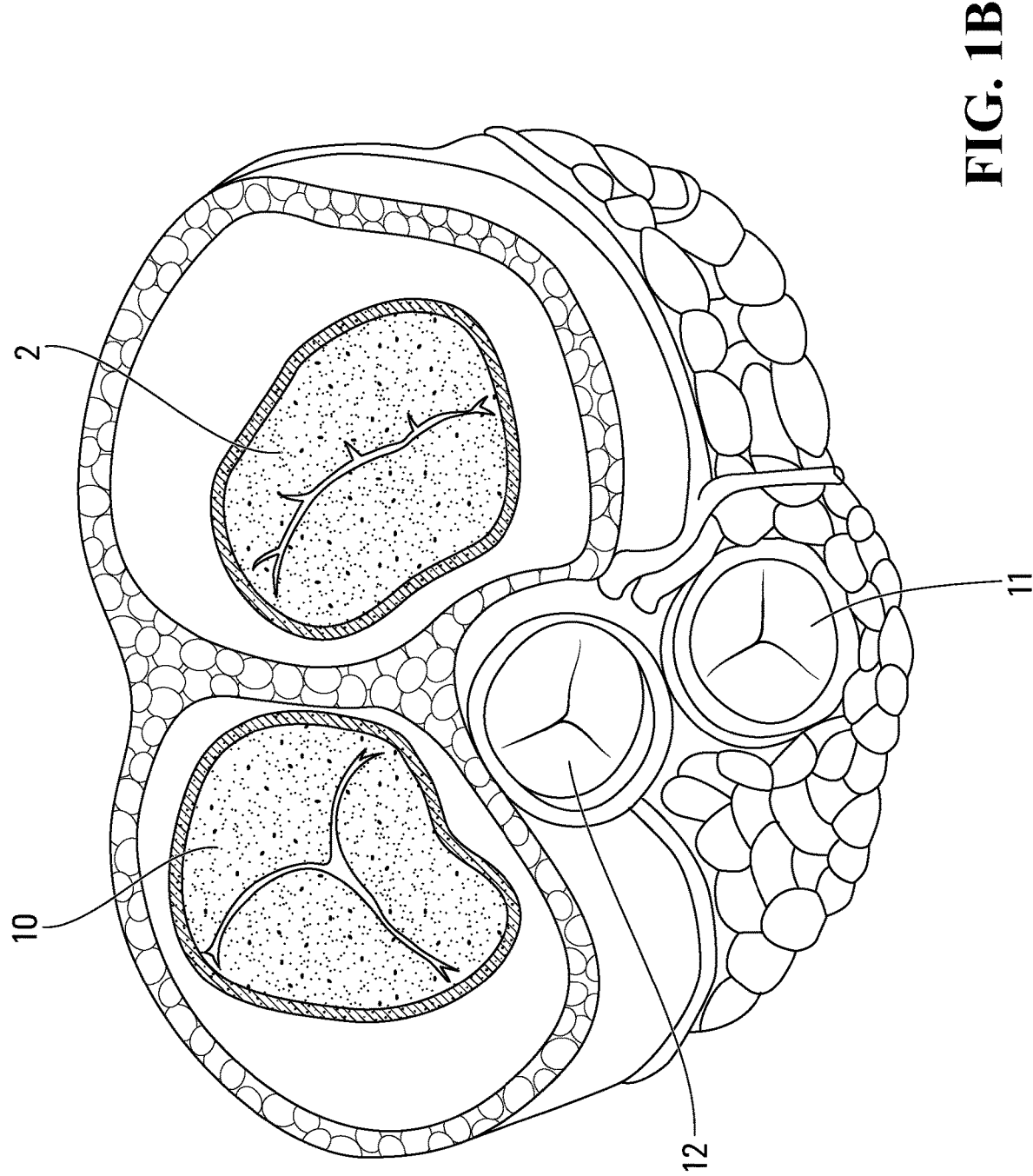

FIGS. 1a and 1b show a two-dimensional cross section of a typical human heart. FIGS. 1a and 1b are referred to herein to better describe where the deflectable sheath 17, focal catheter 60, balloon catheter 18, optical fiber 21 and guidewire 32 may be positioned. Embodiments described herein may be specifically designed to treat any heart valve, such as the mitral valve 2, the tricuspid valve 10, the pulmonary valve 11, and or the aortic valve 12. The devices may be designed to be used in a minimally invasive surgery where the initial entry point can be the femoral vein in the groin, and where the deflectable sheath may be advanced through the inferior vena cava 4, into the right atrium 3. Once in the right atrium 3 the devices may have direct access to the tricuspid valve 10, and with proper deflection mechanism of the sheath 17, focal catheter 60 and balloon catheter 18 proper access is given to the pulmonary valve. For access to the other valves, a transseptal device may be used to cross the septum 5, from the right atrium 3 into the left atrium 6. Once in the left atrium 6, the devices may have direct access to the mitral valve 2 and the aortic valve 12, with proper deflection mechanism on the sheath 17, the focal catheter 60 and the balloon catheter 18.

Figure 2A:
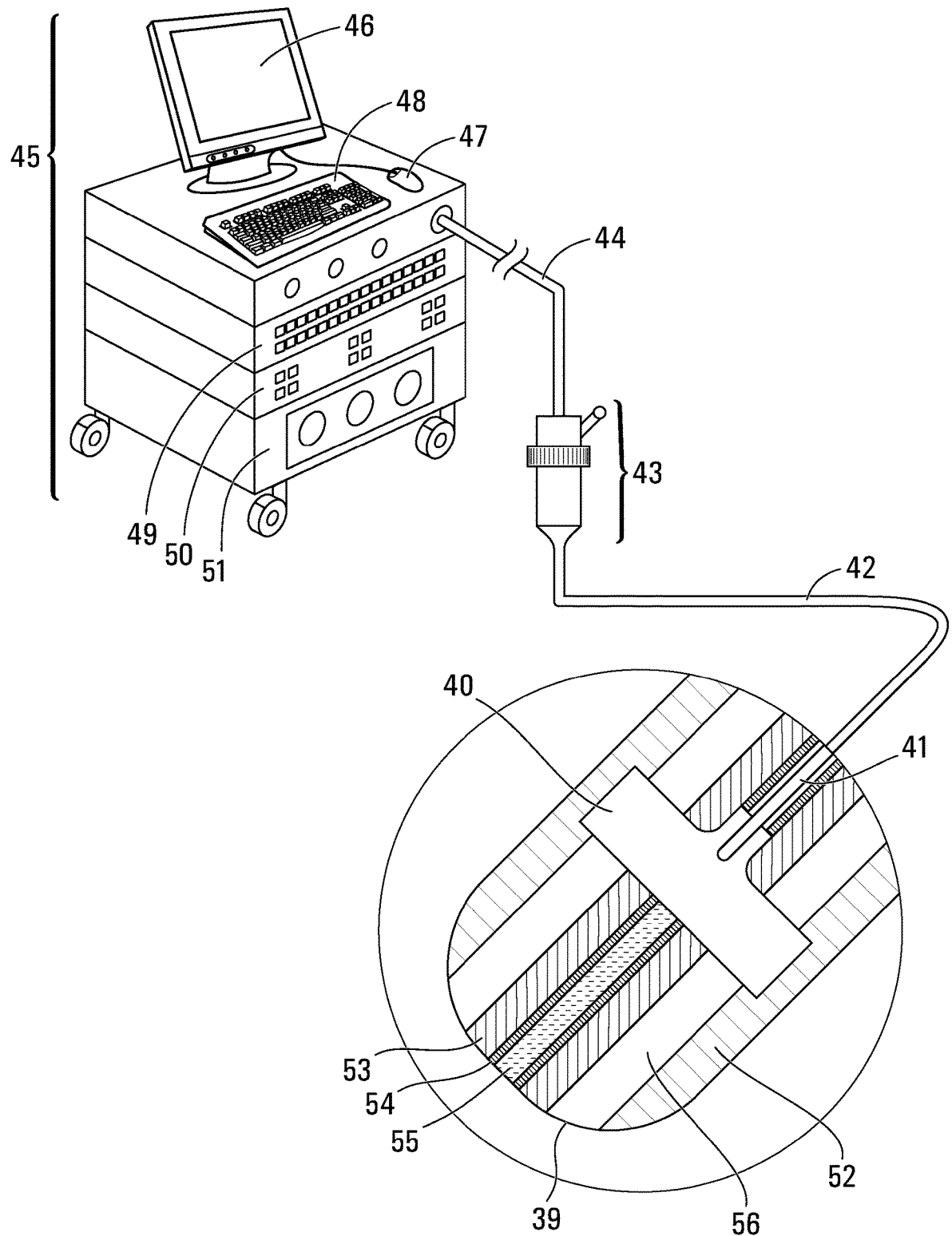
FIG. 2a is an illustration of an exemplary system for performing decalcification or a surgical intervention.
Figure 2B:
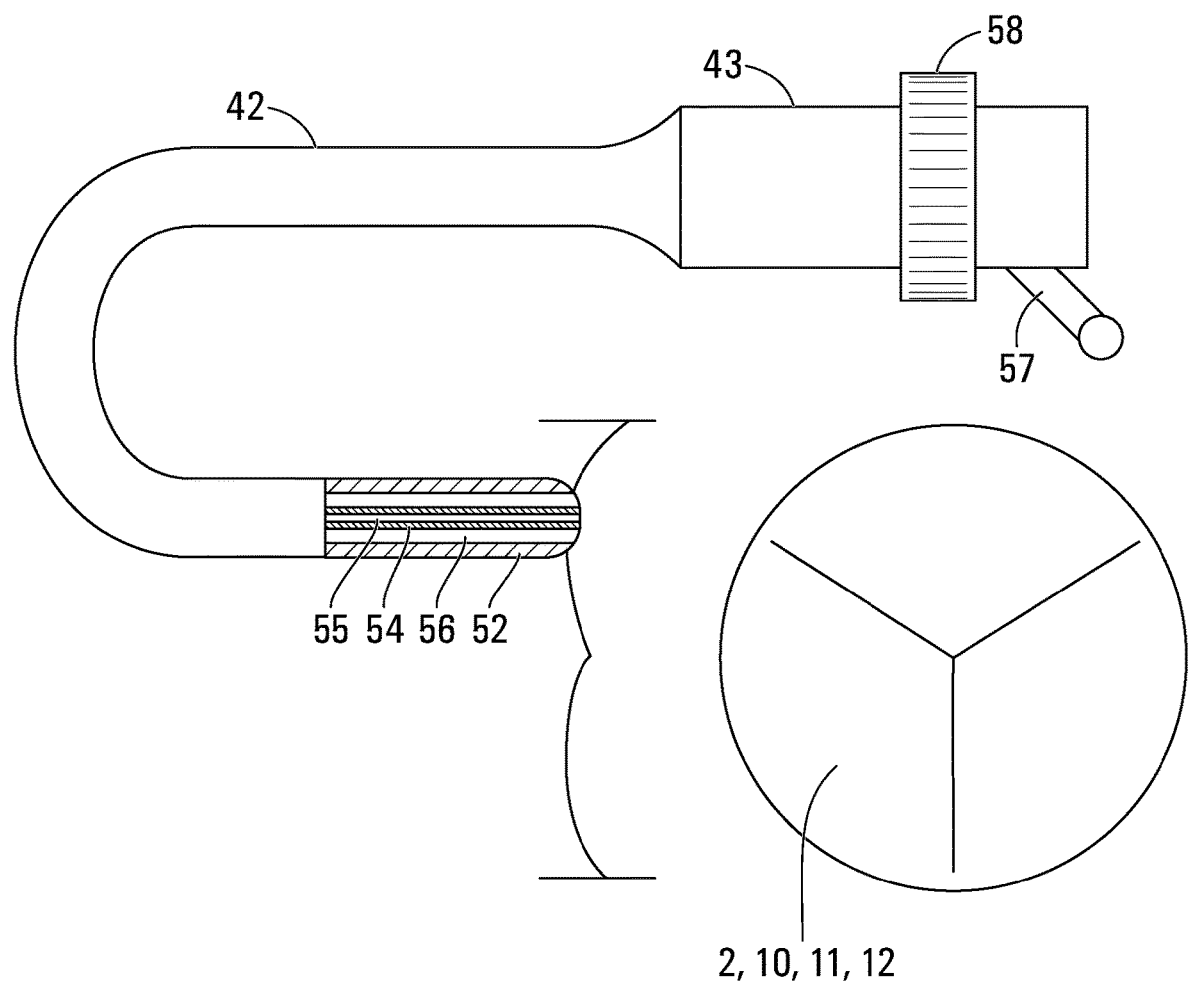
FIG. 2b is an illustration of a heart valve (tricuspid, mitral, aortic pulmonary) with an exemplary diagnostic and treatment focal catheter.
Figure 2C:
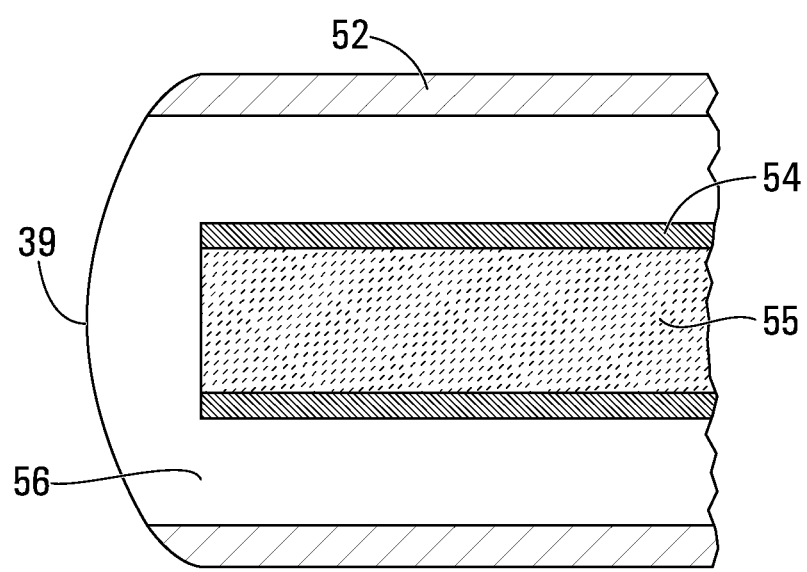
FIG. 2c is an illustration of an axial cross section of the tip of an exemplary diagnostic and treatment focal catheter with a coaxial optical fiber.
Figure 2D:
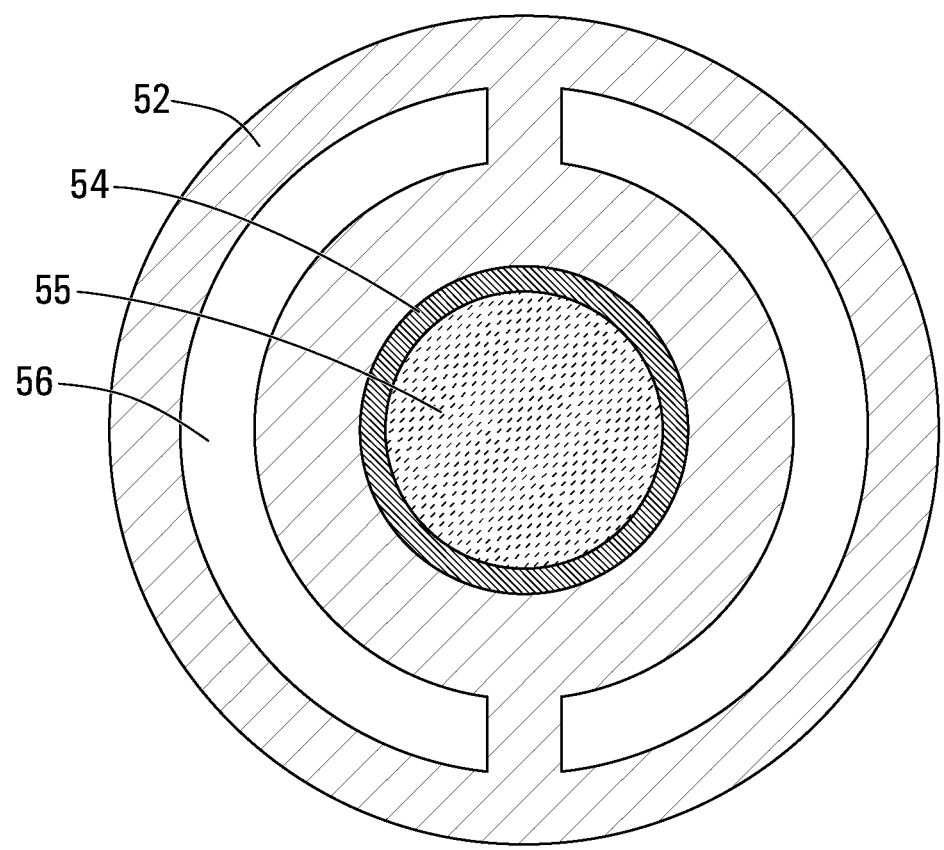
FIG. 2d is an illustration of a radial cross section of the tip of an exemplary diagnostic and treatment focal catheter.
Figure 2E:
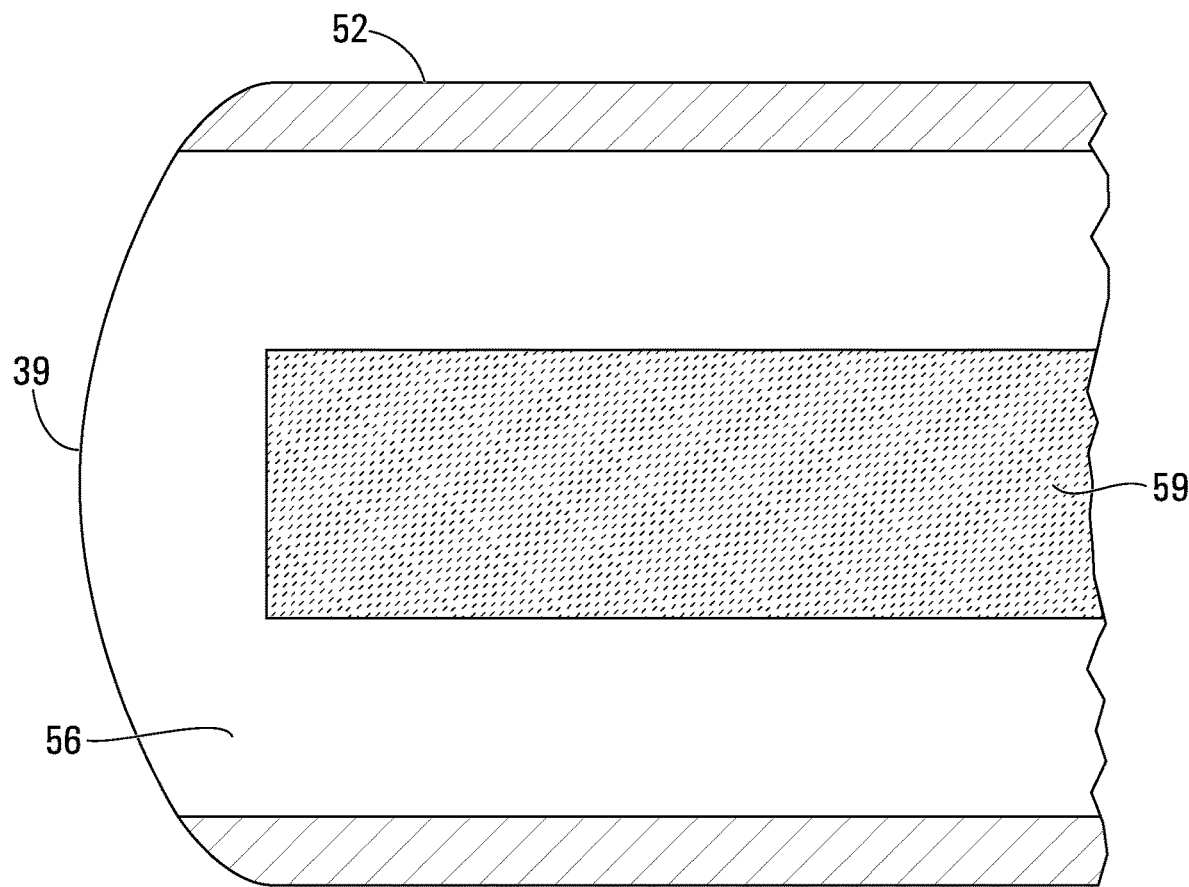
FIG. 2e is an illustration of an axial cross section of the tip of an exemplary diagnostic and treatment focal catheter with a metallic wire

Reference is now made to FIGS. 2a, b, c, d, e, illustrating an exemplary diagnostic and therapeutic system for the diagnosis, detection and treatment of calcium in the cardiovascular system and heart valve leaflet treatment. The system may have a focal catheter that may be advanced near the heart valve to be treated (e.g. 2, 10, 11, 12) and the focal catheter 60 can be guided to the heart valve leaflet with a deflection mechanism 58 in the catheter or sheath handle 43 where, by actuating the deflection mechanism, one or more pull wires are pulling on the pull wire ring assembly 40 to deflect the catheter tip 39 so it can reach the heart valve leaflet. The focal catheter 60 may be connected to the system console that comprises a vacuum pump and its controls 51, an ultrafast laser with harmonic generator and its controls 50, an OCT light source, its controls and a PC 49, a monitor and PC 46, and a user input interface (e.g. a mouse 47 and a keyboard 48). Once tip 39 of the focal catheter 60 is in contact with a heart valve (e.g. 2, 10, 11, 12), the vacuum pump 51 is turned on so the leaflet is sucked onto the tip 39 of the catheter. Once the system has secured the leaflet, OCT module 49 is powered on so that its light source is conveyed though the catheter via the inner core optical fiber 55 so the system 45 can display on the monitor 46 real time tomography. As it is displaying real time tomography, it is mapping the 3d construction of the valve leaflet. The operator can decide to set the system manually for calcification pulverisation or use the integrated algorithm, based on the OCT, to set the ultrafast laser to the optimal setting of the precise and particular site of the pulverisation. The setting can also determine the proper wavelength to safely pulverize the calcium without affecting the native or prosthetic tissue or can be set to human biological tissue pulverisation for anatomy sculpting. Once the system has been properly set to the desired pulverisation mode, the ultrafast laser is actuated and the ultrafast laser beam is carried to the treatment site with the Coaxial Optical fiber outer Core 54. As it is difficult for the OCT technology to penetrate tissue with blood in between, not only does the vacuum suction lumen 56 provide a mean to secure the leaflet, it also permits the OCT system to full penetrate the leaflet for the 3D imaging and calcium detection. Furthermore, the vacuum lumen permits the evacuation of the pulverized nano-particles safely. The system can also be designed to be pulverizing with a metallic wave guidewire 59, using shockwave to mechanically detach the calcium from the leaflet.

For instance, guidewire 69 may be made from Nitinol. The guidewire 59 may have a corkscrew shape that comes into contact with the interior surface of the balloon 20, the balloon 20 holding the leaflets in an open position. The shockwave may be delivered by the sides of the guidewire 59 (the corkscrew portion of the guidewire 59). As such, the shockwave generated by the guidewire 59 travels across the balloon 20, disrupting the neighboring calcium deposits. A fluid medium may not be necessary to carry the shockwaves in the present configuration of guidewire 59, due to the corkscrew configuration of the guidewire 59 that touches the inner surface of the balloon 20.

Figure 3A:
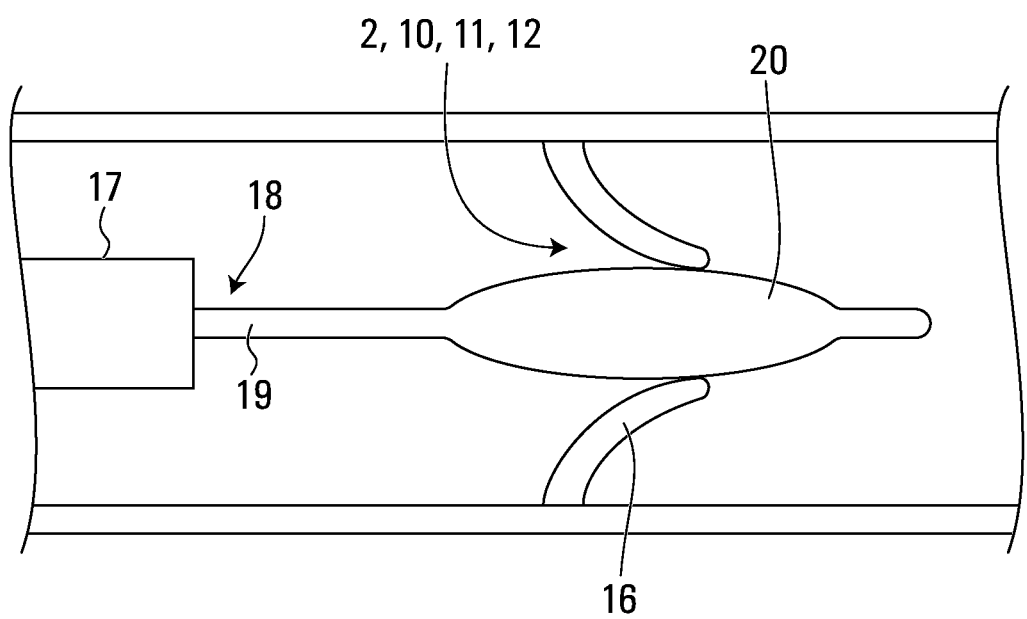
FIG. 3a is a drawing of a heart valve (tricuspid, mitral, aortic, pulmonary) with an exemplary diagnostic and treatment balloon catheter initially inserted though and placed on the heart valve.

Referring now to FIG. 3a, an exemplary deflectable sheath 17 may be advanced near the heart valve to be treated 2, 10, 11, 12 and the balloon catheter 18 may be deployed to be placed through the valve 2, 10, 11, 12 onto the leaflets 16 where the balloon 20 is still in its folded state. The position of the balloon can be adjusted by advancing or retracting the balloon catheter shaft 19.

Figure 3B:
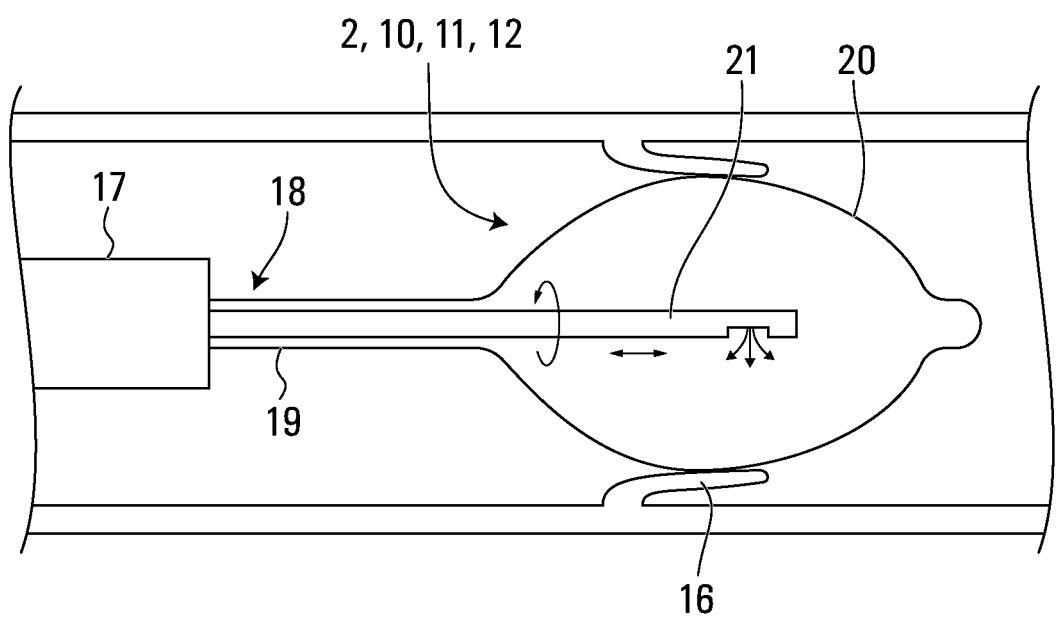
FIG. 3b is a drawing of a heart valve (tricuspid, mitral, aortic, pulmonary) with an exemplary diagnostic and treatment balloon catheter after initial insertion and balloon inflation while placed on the heart valve with OCT visualization optical fiber deployed to verify proper placement.

Referring now to FIG. 3b, an exemplary deflectable sheath 17 may be advanced near the heart valve to be treated 2, 10, 11, 12 and the balloon catheter 18 may be deployed to be placed through the valve 2, 10, 11, 12 onto the leaflets 16 where the balloon 20 may be inflated with liquid or gas. The inflated balloon 20 may start to push the heart valve leaflet 16 into the open position and prevent the leaflets 16 from flapping open and closed. Inflation of the balloon may be performed using a refrigerant so that the leaflets 16, adhere to the balloon, hence securing the leaflets and stabilizing the area.

Figure 3C:
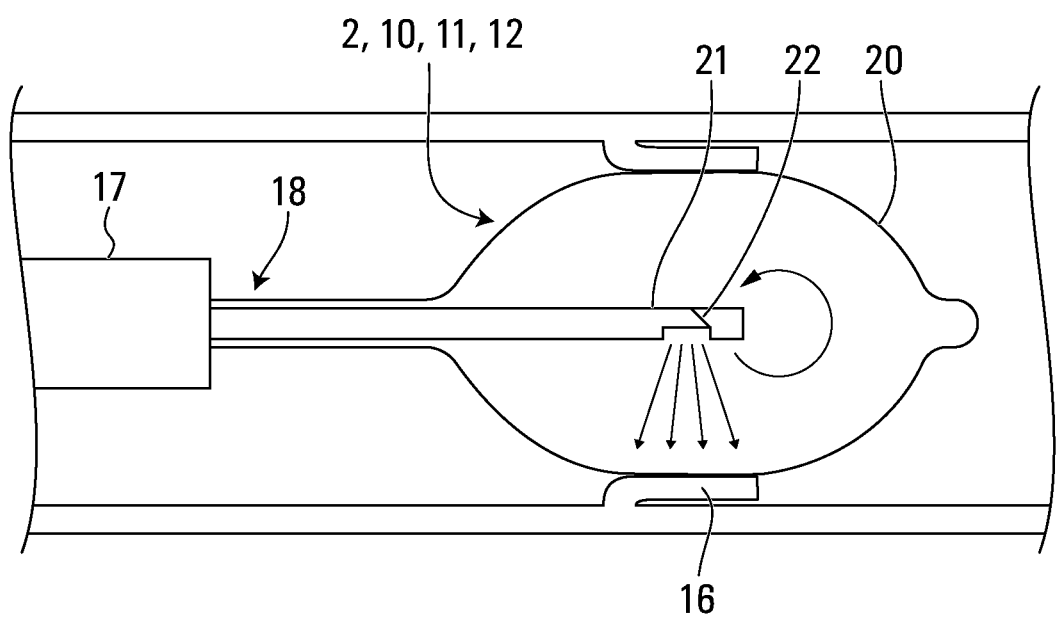
FIG. 3c is a drawing of a heart valve (tricuspid, mitral, aortic, pulmonary) with an exemplary diagnostic and treatment balloon catheter fully deployed and compressing the valve leaflets with OCT visualization optical fiber deployed to perform 3D depth penetrating OCT imaging and subsequent laser ablation with an ultra-fast laser.

As shown in FIG. 3c, an optical fiber 21 with a right-angle prism 22 may be deployed inside the balloon 20 through one of the inner lumens of the catheter. In some embodiments, the distal end of the optical fiber may have the shape of a bulb, a concave prism, convex prism, etc. and can be at various angles (e.g. from 30 degrees to 150 degrees), instead of the distal end having the shape of a right-angle prism.

An imaging laser or superluminescent diode may be directed through the optical fiber 21 and optical coherence tomography imaging may be used to verify proper placement of the balloon 20 onto the leaflets 16. In the event the balloon 20 is improperly placed, the balloon 20 can be deflated and by advancing or retracting the catheter shaft 18, the balloon placement can be adjusted. The balloon may then be re-inflated and the placement verification may be repeated.

Figure 3D:
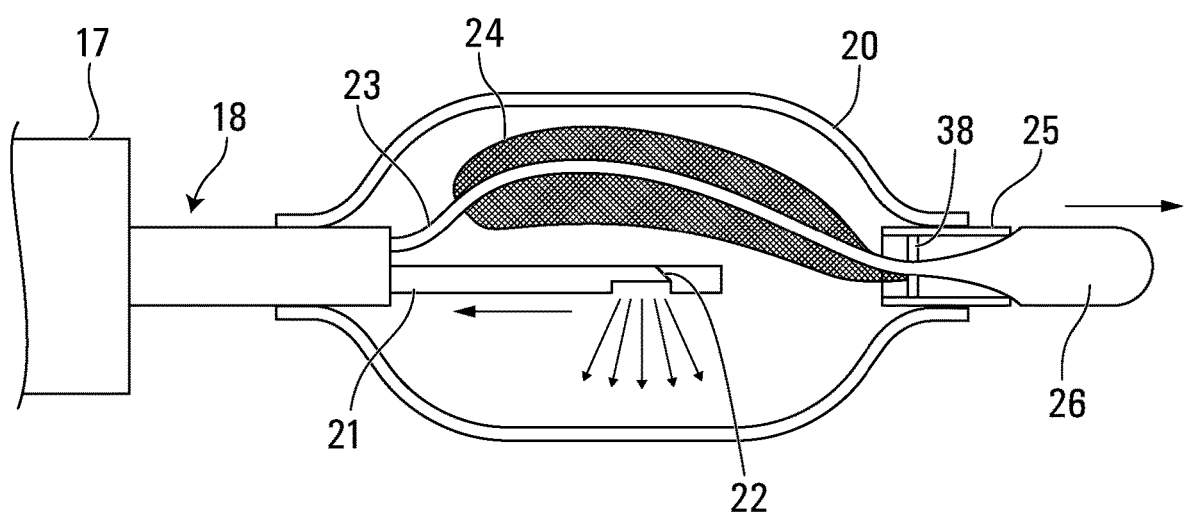
FIG. 3d is a drawing of an exemplary balloon laser ablation catheter with an optical fiber to perform 3D depth penetrating OCT imaging and subsequent laser ablation with an ultra-fast laser, as well as an integrated retracted embolic filter.

Referring now to FIG. 3c, an exemplary deflectable sheath 17 may be advanced near the heart valve to be treated 2, 10, 11, 12 and the balloon catheter 18 may be fully deployed to be placed through the valve 2, 10, 11, 12 onto the leaflets 16. The balloon 20 may be completely filled with liquid or gas and may have pushed the heart valve leaflet 16 into the full open position and may prevent the leaflets 16 from flapping open and shut. Inflation of the balloon may be performed using a refrigerant so that the leaflets 16 adhere to the balloon, hence securing the leaflets and stabilizing the area. An optical fiber 21 with right angle prism 22 may be deployed inside the balloon 20 through one of the catheter inner lumens and an imaging laser or a superluminescent diode may be directed through the optical fiber 21. Optical coherence tomography imaging may be used to locate, identify, and evaluate the valve calcification (location, thickness, density). The imaging source in the fiber may be switched or modified so that an ultrafast laser, such as a femtosecond laser, may be used to pulverize the calcification Referring now to FIG. 3d, an exemplary deflectable sheath 17 with a balloon catheter 18 is shown. The balloon catheter 18 may include an internal embolic filter 24 inside the balloon 20, as well as an imaging and treatment optical fiber 21 with a right angle prism 22. The embolic filter 24 may be attached to the inner shaft 23. The balloon 20 may be bonded or fused on the proximal side onto the balloon catheter shaft 19 and on the distal side onto the balloon bonding outer shaft 25. A hemostatic valve 38 may be located inside the balloon bonding outer shaft 25 to prevent gas or fluid egress and to prevent blood ingress into the catheter 18. The catheter inner shaft may be terminated with an a-traumatic design of the inner shaft tip 26.

Figure 3E:
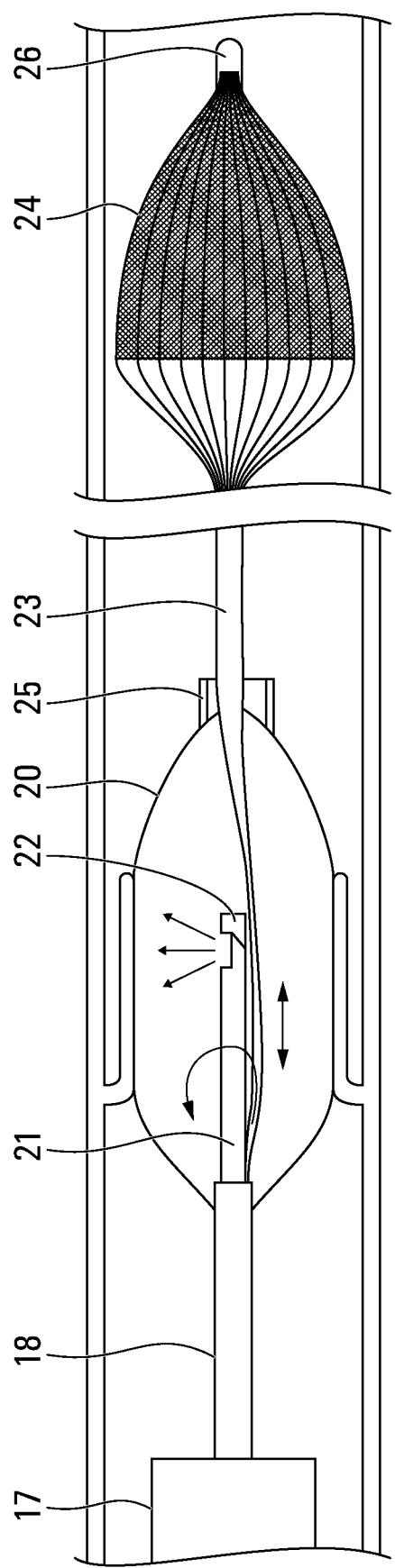
FIG. 3e is a drawing of an exemplary deployed balloon laser ablation catheter with an optical fiber to perform 3D depth penetrating OCT imaging and subsequent laser ablation with an ultra-fast laser, as well as an integrated deployed embolic filter inserted and placed in a heart valve (tricuspid, mitral, aortic, pulmonary)

Referring now to FIG. 3e, an exemplary deflectable sheath 17 may be advanced near the heart valve to be treated 2, 10, 11, 12 and the balloon catheter 18 may be fully deployed to be placed through the valve 2, 10, 11, 12 onto the leaflets 16. The balloon 20 may be completely filled with liquid or gas and may have pushed the heart valve leaflet 16 in the fully open position and may prevent the leaflets 16 from flapping open and shut. Inflation of the balloon may be performed using a refrigerant so that the leaflets 16 adhere to the balloon, hence securing the leaflets and stabilizing the area. An optical fiber with right angle prism 22 may be deployed inside the balloon 20 through one of the catheter inner lumens and an imaging laser or a superluminescent diode may be directed through the optical fiber 21. Optical coherence tomography imaging may be used to locate, identify, and evaluate the valve calcification (location, thickness, density). Prior to treatment, the folded embolic filter 24 may be deployed by pushing on the inner shaft 23. The embolic filter 24 may be pushed through the distal end of the outer shaft 25 distal to the region where the area where the balloon is bonded and through the catheter hemostatic valve 38. The embolic filter 24 may automatically deploy with the minimal blood flow. The imaging source in the fiber may be switched or modified so that an ultrafast laser, such as a femtosecond laser, may be used to pulverize the identified and targeted calcification. OCT is still on in order for the system to parametrically adjust based on results of the pulverization.

The ultrafast laser is a laser capable of transmitting, e.g., pico- and/or femtosecond pulses, where use of the ultrafast laser may result in an a-thermal, or a nearly a-thermal process (considered, in the present disclosure, as being a-thermal).

The ultrafast laser may have an optical fiber (which includes a cable composed of optical fibers) for delivering the light beam. Optical fibers used for beam delivery of an ultrafast laser are known in the art. For instance, reference is made to Bjorn Wedel and Max Funck, "Industrial Fiber Beam Delivery System for Ultrafast Lasers", *Laser Technik Journal*, 4/2016, pages 42 to 44, where an optical fiber with a hollow core structure is described. The micro-structure hollow core fibers support light propagation inside the hollow core (e.g. in a gas or vacuum). However, it will be understood that other optical fibers may be used to propagate a laser beam for an ultrafast laser without departing from the present teachings.

In some exemplary embodiments, the ultrafast laser may include a laser source, the optical fiber, and a coupling unit for adapting the size of the beam and focusing the laser beam to the tip of the optical fiber.

In some examples, the optical fiber 21 used for visualization may also be used as an ultrafast laser for conducting decalcification or for performing surgical intervention carried out on heart tissue. In these examples, for instance, the optical fiber may be a dual body fiber, one with an outer core and inner where the inner core can convey the light used for visualization and the outer core may convey the photon energy. In other examples, the optical fiber may include a dual path fiber. In some examples, the device can alternate between photon emission and imaging. In some examples, the energy reflection of the ultrafast laser function can be used as a light source used for performing optical coherence tomography.

In some examples, the pull wire may be an optical fiber, the pull wire serving for, e.g., propagating light.

Figure 3F:
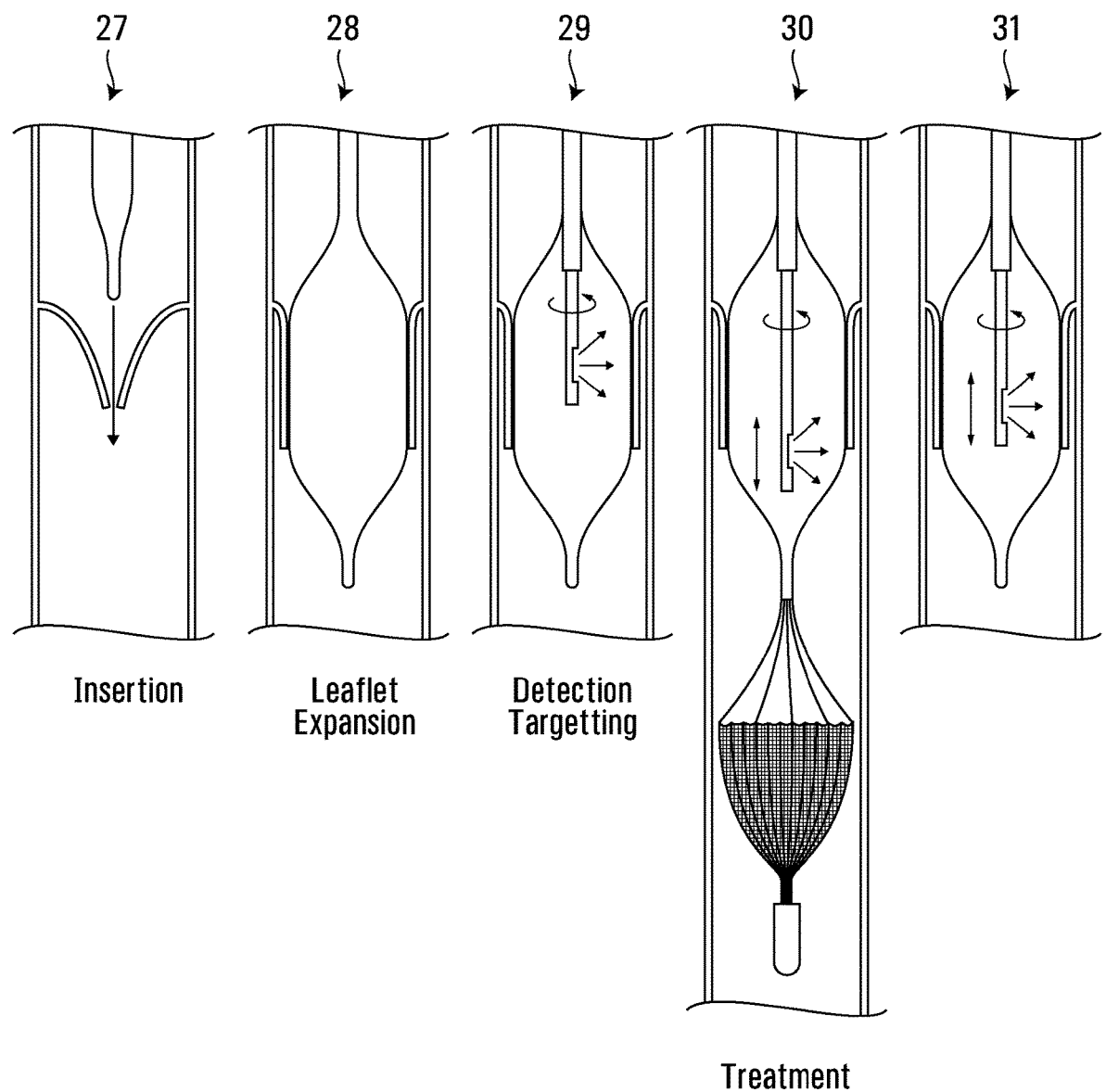
FIG. 3f is a schematic diagram showing the 5 steps to insert, deploy, image, treat, inspect and retract the exemplary balloon laser ablation catheter.

FIG. 3f shows a procedural schematic in which 5 exemplary treatment procedural steps are taken. In step 1 (pictogram 27), the balloon catheter 18 is advanced towards its placement through a heart valve 2, 10, 11, 12. In step 2 (pictogram 28), the balloon 20 is inflated to open the leaflets 16. In step 3 (pictogram 29), the optical fiber 21 is deployed to verify proper placement of the balloon 20 with OCT penetrating imaging. In step 4 (pictogram 30), the balloon 20 is fully inflated and the optical fiber 21 is detecting, evaluating and mapping the targeted area with density evaluation. The embolic filter 24 is deployed, the laser source is modified or switched to an ultrafast laser, such as a pico or femto second laser, and is performing laser pulverization of calcium with parametric control. In step 5 (pictogram 31) the pulverization is completed and stopped, the embolic filter 24 is retracted, and the optical fiber 21 is used to perform a post treatment evaluation.

Figure 4A:
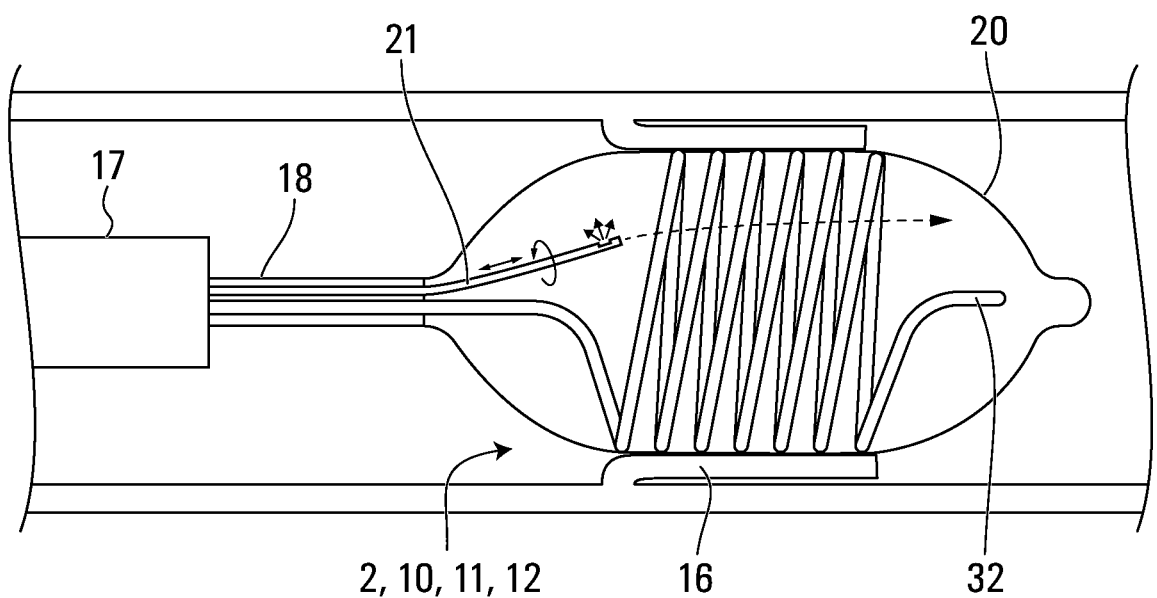
FIG. 4a is a drawing of a balloon, a wire shockwave ablation, and an exemplary catheter with an optical fiber to perform 3D depth penetrating OCT imaging, laser treatment and subsequent post treatment imaging.

FIG. 4a shows an exemplary deflectable sheath 17 with a balloon catheter 18. The balloon catheter 18 may include an internal Nitinol guidewire 32 inside the balloon 20 as well as an imaging and treatment optical fiber 21 with a right angle prism 22. Nitinol guidewire 32 may be deployed through one of the balloon catheter lumen. During deployment the guidewire 32, due to the superelastic property of Nitinol, may be passed through a straight lumen but when it come out inside the balloon 21, the guidewire coils may push the balloon 20 against the valve 2, 10, 11,12 further after inflation. The guidewire 32 may be used as a mechanical shockwave guide to detach the calcification from the valve leaflets 16.

Figure 4B:
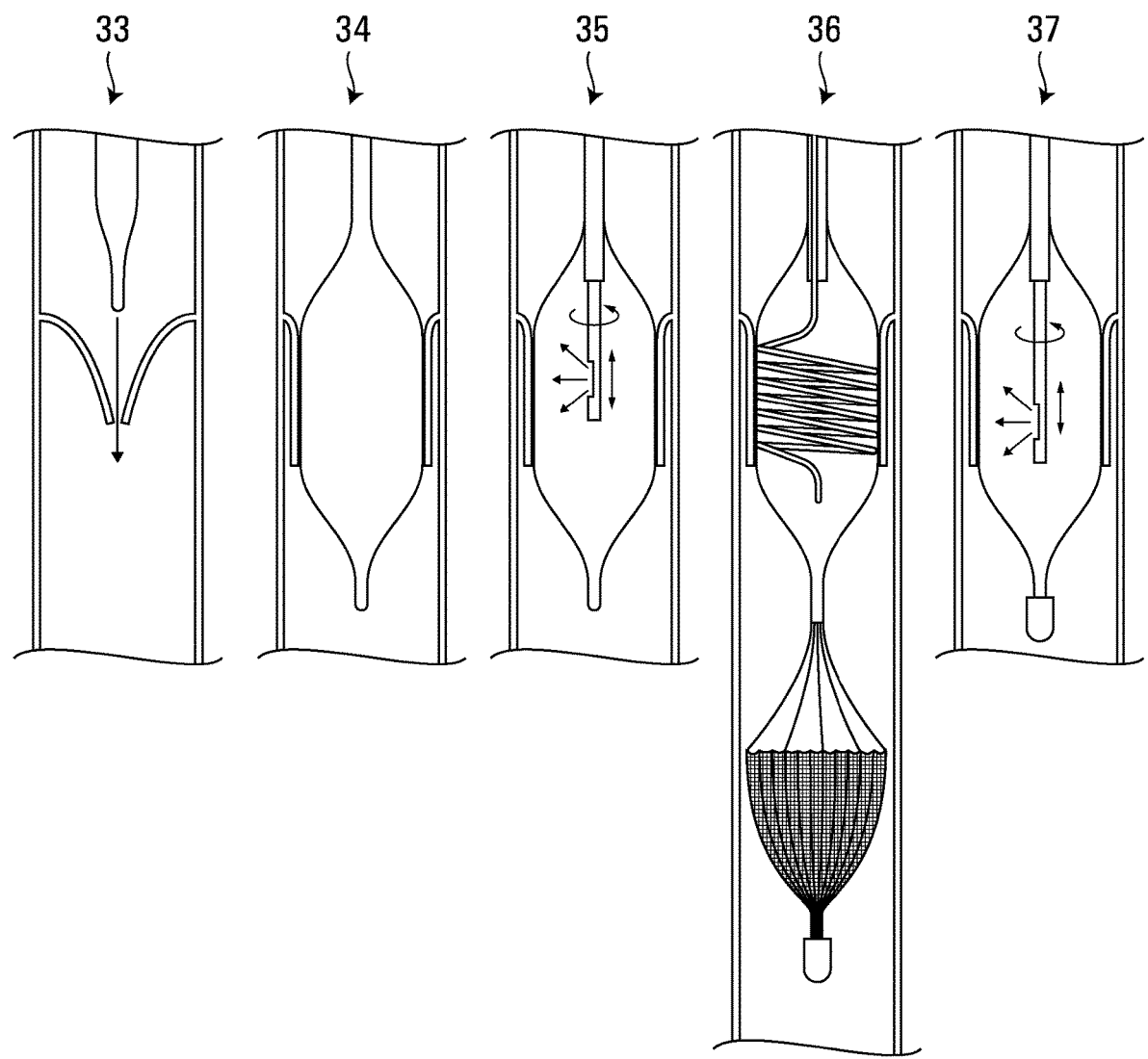
FIG. 4b is a schematic diagram showing 5 steps to insert, deploy, image, treat, inspect and retract the exemplary balloon, wire shockwave ablation, catheter with an imaging optical fiber.

FIG. 4b shows a procedural schematic in which 5 exemplary treatment procedural steps are taken. In step 1 (pictogram 33), the balloon catheter 18 is advanced towards its placement through a heart valve 2, 10, 11, 12. In step 2 (pictogram 34), the balloon 20 is inflated to open the leaflets 16. In step 3 (pictogram 35) the optical fiber 21 is deployed to verify proper placement of the balloon 20 with OCT penetrating imaging. In step 4 (pictogram 36), the balloon 20 is fully inflated; the optical fiber 21 is detecting, evaluating, and mapping the targeted area with density evaluation. The embolic filter 24 is deployed, the Nitinol coiled shockwave guidewire 32 is deployed, and a shockwave is disseminated thought the guidewire 32 to detach the calcium. In step 5 (pictogram 37) the treatment is completed and stopped, the embolic filter 24 is retracted, and the optical fiber 21 is used to perform a post treatment evaluation.

Figure 5:
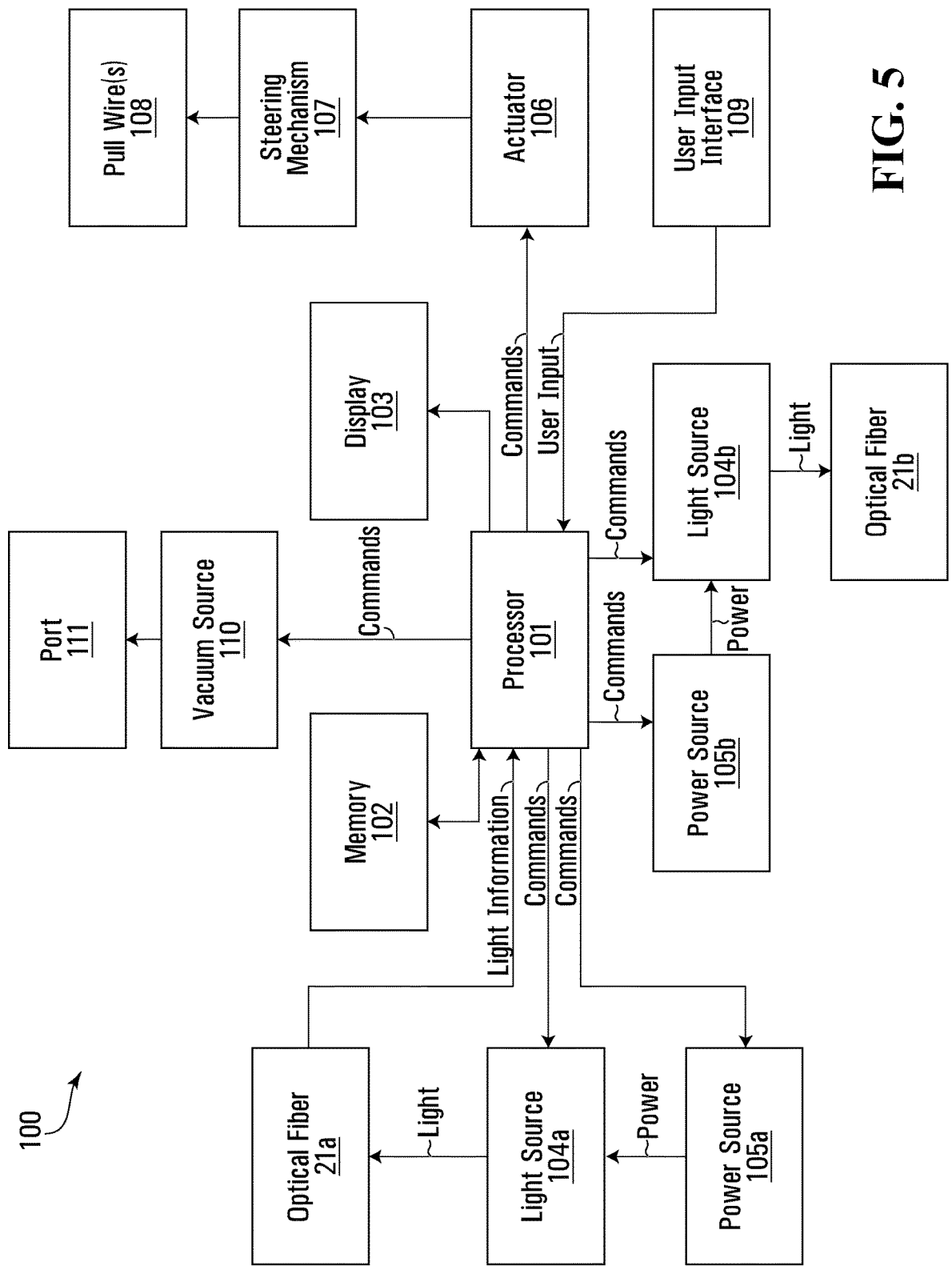
FIG. 5 is a block diagram of an exemplary system for conducting visualization and performing decalcification and/or a surgical intervention on heart tissue.

Exemplary System for Decalcifying Heart Tissue and/or Performing a Surgical Intervention Targeting Heart Tissue:

Reference is now made to FIG. 5, illustrating an exemplary system 100 for decalcifying heart tissue and/or for performing a surgical intervention targeting heart tissue. For greater clarity, heart tissue may include the coronary arteries.

The system 100 includes a processor 101, memory 102, a power source 105b for powering a laser source 104b, an optical fiber 21b for propagating a laser beam generated by the laser source 104b, a power source 105b for powering a light source 104a, and an optical fiber 21b for propagating light from the light source 104a.

The system 100 may have an actuator 106 for, e.g., electrically, mechanically or pneumatically controlling the steering mechanism 107 of a deflectable sheath or catheter, the steering mechanism 107 causing deflection of the tip of a shaft of the sheath or catheter by applying or removing tension from the one or more pull wires 108 of the sheath or catheter.

The system 100 may have a vacuum source 110 (e.g. vacuum pump) for connecting to a port 111 of the catheter, sheath or dilator.

The controller of the system 100 (e.g. the processor 101 and memory 102, with program code stored in memory 102) may cause the vacuum source 110 to turn on (and/or reducing or increasing the strength of the vacuum). As such, the vacuum source 100 creates a vacuum in a lumen of the catheter, sheath or dilator, as the port 111 interfaces between the lumen and the vacuum source 110. The vacuum created in the lumen can be used to remove, through the lumen, pulverized calcium particulates or debris, or to secure heart tissue to the catheter, sheath or dilator.

The system 100 may have a user input interface 109 and a display 103.

The processor 101 and memory 102 may be connected via, e.g., a BUS, where the processor 101 carries out instructions by executing program code stored in the memory 102.

The memory 102 is a storage medium for storing program code and data that is retrievable by the processor 101.

The processor 101 and the memory 102 may be referred to herein as a controller.

The user input interface 109 receives input from a user to, e.g., turn on/off power source 105a, power source 106b, adjust the properties of the laser source 104b, control the steering mechanism 107 via the actuator 106, etc. The user input interface 109 may be, e.g., a touchscreen, a keyboard, a mouse, a microphone, a button, etc.

The display 103 may be a screen for showing certain images to the user, such as the image of the surgical site generated by optical coherence tomography, allowing the user to, e.g., view the progress of the decalcification or surgical intervention.

The steering mechanism 107 may be integrated or present in the handle of the catheter/sheath. The steering mechanism, and/or the catheter, sheath, dilator, may be integrated or part of a robot that is computer-controlled, such as a surgical robot as is known in the art.

The one or more pull wires 108 are located in the shaft of the catheter and/or sheath, and attached to or near the distal end of the shaft. The properties of the one or more pull wires 108 and the positioning of the one or more pull wires 108 within the shaft of the catheter or sheath are as is known in the art for a deflectable catheter or sheath.

The power source 105a (e.g. an electrical outlet, a battery, etc.) provides power to the light source 104a. The light source 104a generates light that is propagated by the optical fiber 21a.

In the present disclosure, by optical fiber, it is meant an optical fiber or a bundle of optical fibers that may be encased in a housing (e.g. forming a cable).

The optical fiber 21a projects light on a nearby surface to conduct a surgical intervention or decalcification. Light reflection is then used to provide information to the processor 101 to conduct visualization of the site using optical coherence tomography. Optical coherence tomography may be achieved by using processes as are known in the art.

Power source 105b (e.g. an electrical outlet, a battery, etc.) provides power to the laser source 104b. The laser source 104b may be one as is known in the art to provide an ultrafast laser beam (at or below a few picoseconds pulse durations, where the processing by the laser beam is an a-thermal process). The laser beam produced by the laser source 104b may then be propagated by the optical fiber 21b to the target site for decalcifying and/or conducting the surgical intervention on heart tissue.

It will be understood that, as explained herein, there may be a single power source 105 for powering light source 104a and laser source 105b. There may be a single light or laser source 104 and optical fiber 21 for generating and propagating photons for either visualization or laser processing (e.g. cutting, pulverization) as explained herein, where, e.g., the properties of the laser source 104 may be adapted by the processor 101 as a function of the desired function (visualization or laser processing).

During the course of the decalcifying and/or the surgical intervention, the processor 101 may generate data using optical coherence tomography, based on the light information provided by the optical fiber 21a, to further adjust the properties of the laser source 104b, such as the pulse duration, the light wavelength, etc., or to change the laser source 104b.

In some embodiments, the data generated by the processor 101 using optical coherence tomography may be used to obtain depth information pertaining to the site of the calcium buildup or the site of the surgical intervention. The processor 101 may then generate commands directed to the laser source 104b to modify, e.g., the laser focal distance.

Figure 6:
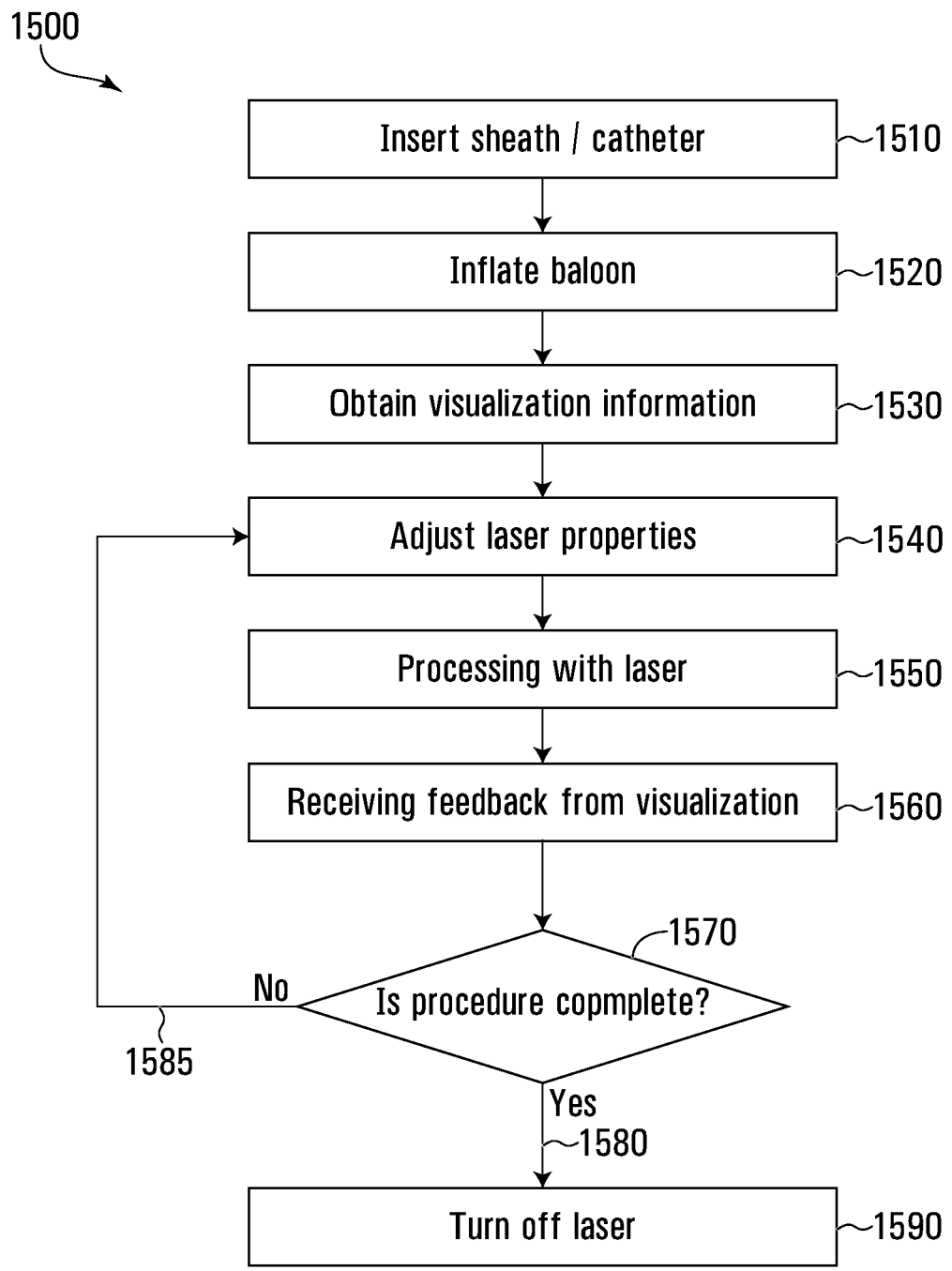
FIG. 6 is a flowchart diagram of an exemplary method of decalcifying heart tissue and/or performing a surgical intervention on heart tissue using an ultrafast laser.

Exemplary Method of Decalcifying and/or Performing a Surgical Intervention on Heart Tissue:

Reference is now made to FIG. 6, illustrating an exemplary method 1500 for decalcifying heart tissue and/or performing a surgical intervention on heart tissue.

The sheath and/or catheter is inserted into the patient at step 1510.

A balloon of a dilator may be inserted into the patient, where the balloon may be inflated to press a valve leaflet open such that the valve leaflet does not flap open and closed at step 1520.

An optical fiber that is inserted into the patient (e.g. contained in the shaft of the catheter or sheath) may be used to propagate light from a light source to the site of the cardiac procedure, the light exiting the optical fiber and projecting onto heart tissue. Visualization information is obtained from the behavior of the light as it reaches surrounding surfaces (e.g. heart tissue, calcium deposits) through optical coherence tomography at step 1530.

The visualization information is used to adjust the ultrafast laser properties, such as its position, its pulse duration, wavelength, focal distance, laser source, etc., based, e.g., on the properties of the site of the surgical intervention or calcium (e.g. size, density, tissue properties, distance separating exit point of laser beam and target site for decalcifying and/or surgical intervention, etc.) at step 1540.

The laser is then processed to pulverize the calcium and/or perform the surgical intervention (e.g. a-thermal ablation, cutting, etc.) at step 1550.

During the laser processing, visualization information may be regularly generated by the light information (the light being generated by the light source during the laser processing), providing feedback information on the laser processing at step 1560.

The feedback visualization information may be used to determine if the decalcifying based on surgical procedure is complete at step 1570, or if properties of the laser are to be adjusted during the procedure.

If the procedure is not complete at step 1585, as a function of the visualization information, additional properties of the ultrafast laser may be adjusted at step 1540, where steps 1540-1570 are repeated until the procedure is complete.

If the procedure is complete at step 1580, the laser may be turned off at step 1590.

Although the invention has been described with reference to preferred embodiments, it is to be understood that modifications may be resorted to as will be apparent to those skilled in the art. Such modifications and variations are to be considered within the purview and scope of the present invention.

Representative, non-limiting examples of the present invention were described above in detail with reference to the attached drawing. This detailed description is merely intended to teach a person of skill in the art further details for practicing preferred aspects of the present teachings and is not intended to limit the scope of the invention. Furthermore, each of the additional features and teachings disclosed above and below may be utilized separately or in conjunction with other features and teachings.

Moreover, combinations of features and steps disclosed in the above detailed description, as well as in the experimental examples, may not be necessary to practice the invention in the broadest sense, and are instead taught merely to particularly describe representative examples of the invention. Furthermore, various features of the above-described representative examples, as well as the various independent and dependent claims below, may be combined in ways that are not specifically and explicitly enumerated in order to provide additional useful embodiments of the present teachings.

Numerals referred to in the Figures:
1) Heart
2) Mitral Valve
3) Right atrium
4) Inferior vena cava
5) Septum
6) Left atrium
7) Left ventricle
8) Superior vena cava
9) Aorta
10) Tricuspid valve
11) Pulmonary valve
12) Aortic Valve
13) Pulmonary veins
14) Right ventricle
15) Pulmonary artery
16) Valve leaflet
17) Deflectable sheath
18) Balloon catheter
19) Balloon catheter shaft
20) Balloon
21) Optical fiber with right angle prism for OCT depth penetrating visualization and ultra-fast laser treatment
22) Right angle prism
23) Inner shaft
24) Embolic filter
25) Outer shaft balloon bonding
26) Inner shaft tip
27) Initial insertion schematic, laser treatment
28) Initial balloon inflation schematic, laser treatment
29) Initial detection and targeting schematic, laser treatment
30) Embolic filter deployment and laser treatment schematic, laser treatment
31) Final imaging post treatment schematic, laser treatment
32) Nitinol coiled waveguidewire
33) Initial insertion schematic, waveguidewire shockwave treatment
34) Initial balloon inflation schematic, waveguidewire shockwave treatment
35) Initial detection and targeting schematic, waveguidewire shockwave treatment
36) Embolic filter deployment and waveguidewire shockwave treatment schematic, waveguidewire shockwave treatment
37) Final imaging post treatment schematic, waveguidewire shockwave treatment
38) catheter Hemostatic valve
39) Focal catheter tip
40) Focal catheter pull wire ring assembly
41) Focal catheter pull wires
42) Focal catheter shaft
43) Focal catheter handle with deflection mechanism
44) Focal catheter Coaxial cable (dual core fiber, vacuum)
45) Console (Controls, keyboard, mouse, monitor, Vacuum, Ultrafast fiber laser, OCT light source, harmonic generator,
46) Monitor
47) Mouse
48) Keyboard
49) OCT light source, controls, PC,
50) Ultra fast laser and controls
51) Vacuum pump an controls
52) Focal Catheter shaft outer wall
53) Focal catheter shaft inner wall
54) Coaxial Optical fiber outer core
55) Coaxial Optical fiber inner core
56) Focal catheter shaft vacuum lumen
57) Focal catheter side port 58) Focal catheter deflection knob or thumb wheel
59) Metallic wave-guide-wire
60) Focal catheter

What is claimed is:

1. A deflectable sheath or dilator or catheter used for cardiac procedures comprising:
   a shaft with a proximal end and a distal end comprising one or more lumens running along a length of said shaft;
   an optical fiber located in one of said one or more lumens for use in channeling light used for visualization of calcification, heart tissue architecture or the progress of the cardiac procedure by performing 3D depth penetrating optical coherence tomography;
   wherein:
      said sheath or dilator or catheter further comprises an additional optical fiber for use as part of an ultrafast laser for calcium removal on or in heart valve tissue or for performing surgical intervention of the heart, said additional optical fiber running along a length of another of said one or more lumens; or
      said optical fiber is configurable for propagating a photon beam as part of an ultrafast laser for removing calcium on or in heart valve tissue or for performing surgical intervention of the heart; and
   a controller that is configured to:
      generate calcium density data by said performing optical coherence tomography, said calcium density data providing information on a location of a site for the surgical intervention or of the calcium deposit; and
      cause an adjustment of one or more of pulse duration, wavelength, focal distance, laser source of the ultrafast laser based on the calcium density data.

2. The deflectable sheath or dilator or catheter as defined in claim 1, further comprising the additional optical fiber for use as part of an ultrafast laser for calcium removal on or in heart valve tissue or for performing surgical intervention of the heart, said additional optical fiber running along a length of another of said one or more lumens.

3. The deflectable sheath or dilator or catheter as defined in claim 2, wherein said additional optical fiber is a hollow core optical fiber.

4. The deflectable sheath or dilator or catheter as defined in claim 1, wherein said optical fiber is configurable for propagating a photon beam as part of an ultrafast laser for removing calcium on or in heart valve tissue or for performing surgical intervention of the heart, wherein said optical fiber is a dual body optical fiber comprising an inner core and an outer core, wherein the outer core of the dual body optical fiber is a hollow core optical fiber, wherein said visualization is carried out by said inner core, and said calcium removal or said surgical intervention of the heart is performed by photon energy transported by said outer core.

5. The deflectable sheath or dilator or catheter as defined in claim 1, further comprising:
   a port for connecting said deflectable sheath or dilator or catheter to a vacuum source; and
   an additional lumen with a coaxial structure running along a length of said shaft for removing pulverized calcium or other debris through said additional lumen, or for securing a valve leaflet in an open position, when said deflectable sheath or dilator or catheter is connected to said vacuum source through said port.

6. The deflectable sheath or dilator or catheter as defined in claim 1, wherein an end of said optical fiber used for visualization located at or near said distal end of said shaft has a right-angle prism configuration.

7. The deflectable sheath or dilator or catheter as defined in claim 1, wherein the controller is further configured to perform at least one of:
   receive light information from light that was first emitted by said optical fiber, and perform optical coherence tomography based on said light information; and
   select regions for decalcification or for performing surgical intervention as a function of data obtained by said performing optical coherence tomography.

8. A surgical robot comprising the deflectable sheath or dilator or catheter of claim 1.

9. The deflectable sheath or dilator or catheter as defined in claim 1, further comprising an inflatable balloon at the distal end of the shaft for pressing a heart valve leaflet in an open position.

10. The deflectable sheath or dilator or catheter as defined in claim 1, further comprising:
    one or more pull wires running along a length of the shaft; and
    a steering system for causing tension to be applied to or diminished from one or more of the one or more pull wires for steering the shaft, wherein each of the or more pull wires is connected or connectable to a steering mechanism.

11. The deflectable sheath or dilator or catheter as defined in claim 10, further comprising a handle joined to the proximal end of the shaft, wherein the steering system is located in the handle and comprises an input interface for allowing a user to manually actuate the steering mechanism.

12. The deflectable sheath or dilator or catheter as defined in claim 1, further comprising an embolic filter.

13. The deflectable sheath or dilator or catheter as defined in claim 1, further comprising a power source for one of:
    powering the ultrafast laser; and
    when the optical fiber is configurable for propagating a photon beam as part of an ultrafast laser, providing a source of power for generating the photon beam.

* * * * *